(12) United States Patent
Combadiere et al.

(10) Patent No.: US 8,956,617 B2
(45) Date of Patent: Feb. 17, 2015

(54) VACCINATION BY TRANSCUTANEOUS TARGETING

(75) Inventors: Behazine Combadiere, Magny le Hongre (FR); Annika Vogt, Berlin (DE); Ulrike Blume-Peytavi, Berlin (DE); Brigitte Autran, Paris (FR); Christine Katlama, Paris (FR); Hans Schaeffer, Berlin (DE)

(73) Assignees: Fondation Bettencourt-Schueller, Paris (FR); Universite Pierre et Marie Curie Paris 6, Paris (FR); Universite Charite—Universitaetsmedizin Berlin, Berlin (DE)

(*) Notice: Subject to any disclaimer, the term of this patent is extended or adjusted under 35 U.S.C. 154(b) by 1838 days.

(21) Appl. No.: 11/993,737

(22) PCT Filed: Jun. 23, 2006

(86) PCT No.: PCT/IB2006/002417
§ 371 (c)(1),
(2), (4) Date: May 19, 2010

(87) PCT Pub. No.: WO2006/136959
PCT Pub. Date: Dec. 28, 2006

(65) Prior Publication Data
US 2010/0285099 A1 Nov. 11, 2010

(30) Foreign Application Priority Data
Jun. 23, 2005 (FR) ...................................... 05 06412

(51) Int. Cl.
A61K 39/00 (2006.01)
A61K 9/00 (2006.01)
A61K 9/50 (2006.01)
(Continued)

(52) U.S. Cl.
CPC ............. *A61K 9/0014* (2013.01); *A61K 9/5084* (2013.01); *A61K 39/12* (2013.01); *A61K 38/00* (2013.01); *A61K 9/0021* (2013.01); *A61K 9/51* (2013.01); *A61K 9/14* (2013.01); *A61K 39/00* (2013.01);
(Continued)

(58) Field of Classification Search
None
See application file for complete search history.

(56) References Cited

U.S. PATENT DOCUMENTS 5,589,466 A * 12/1996 Felgner et al. .............. 514/44 R
5,716,637 A * 2/1998 Anselem et al. .............. 424/450
(Continued)

FOREIGN PATENT DOCUMENTS

| WO | WO 03/103570 | * 12/2003 |
| WO | 2004 012657 | 2/2004 |
| WO | 2004 084939 | 10/2004 |

OTHER PUBLICATIONS

Roy, et al. Induction of antigen-specific CD8+ T cells, T helper cells, and protective levels of antibody in humans by particle-mediated administration of a hepatitis B virus DNA vaccine. Vaccine. 2001; 19 (7-8): 764-778.*

(Continued)

*Primary Examiner* — Zachariah Lucas
*Assistant Examiner* — Stuart W Snyder
(74) *Attorney, Agent, or Firm* — Oblon, Spivak, McClelland, Maier & Neustadt, L.L.P.

(57) ABSTRACT

The present invention relates to a method of vaccination via hair follicles that makes it possible to target vaccine components to the antigen-presenting cells in order to induce a protective and effective immune response against pathogens.

20 Claims, 16 Drawing Sheets

(51) Int. Cl.
    *A61K 39/12*    (2006.01)
    *A61K 38/00*    (2006.01)
    *A61K 9/51*     (2006.01)
    *A61K 9/14*     (2006.01)

(52) U.S. Cl.
    CPC .......... *A61K 2039/54* (2013.01); *Y10S 977/773* (2013.01)
    USPC ...................................... 424/184.1; 977/773

(56) References Cited

U.S. PATENT DOCUMENTS

| | | |
|---|---|---|
| 6,355,271 B1 | 3/2002 | Bell et al. |
| 6,358,242 B1* | 3/2002 | Cecchetti ........................... 606/9 |
| 6,436,402 B1* | 8/2002 | Zhao et al. ................. 424/189.1 |
| 2001/0048925 A1 | 12/2001 | Bell et al. |
| 2003/0190308 A1* | 10/2003 | Braun et al. ................. 424/93.2 |
| 2005/0106226 A1* | 5/2005 | Cormier et al. ............... 424/449 |

OTHER PUBLICATIONS

FollicleOpeningTechniques.pdf; google search results from Nov. 18, 2011 by sws.*

Hammond, et al. Transcutaneous immunization of domestic animals: opportunities and challenges. Adv. Drug. Delivery. 2000; 43: 45-55.*

Peachman, et al. Immunization with DNA through the skin. Methods. 2003; 31(3): 232-242.*

Roy, Michael J. et al., "Induction of antigen-specific CD8 + T cells, T helper cells, and protective levels of antibody in humans by particle-mediated administration of a hepatitis B virus DNA vaccine", Vaccine, vol. 19, No. 7-8, pp. 764-778, 2000.

* cited by examiner

FIG. 13

| | Transcutaneous | | | Intramuscular | | |
|---|---|---|---|---|---|---|
| | Day 0 | Day 14 | Day 28 | Day 0 | Day 14 | Day 28 |
| n | 6 | 6 | 6 | 4 | 4 | 4 |
| median | 76.5 | 234.0 | 266.5 | 132.5 | 340.5 | 447.0 |
| IQR | 160 | 130 | 280 | 290 | 88 | 486.5 |
| Fold Increase | — | 3.0 | 2.6 | — | 3.0 | 3.8 |

IFNγSFU/million of PBMCs

Non-parametric Mann-Wihtney   $p=0.17$   $p=0.35$

FIG. 15A

| | Transcutaneous | | | Intramuscular | | |
|---|---|---|---|---|---|---|
| | % IFNγ+ amoung CD4 cells | | | % IFNγ+ amoung CD4 cells | | |
| | Day 0 | Day 14 | Day 28 | Day 0 | Day 14 | Day 28 |
| n | 6 | 6 | 6 | 4 | 4 | 4 |
| Median | 0.03 | 0.10 | 0.12 | 0.00 | 0.36 | 0.16 |
| IQR | 0.1 | 0.04 | 0.04 | 0.18 | 0.24 | 0.38 |
| positive responses | 3/6 | 6/6 | 6/6 | 1/4 | 4/4 | 3/4 |
| Non-parametric Mann-Withney test | | p=0.01 | | | ns | |

FIG. 15B

| | Transcutaneous | | | Intramuscular | | |
|---|---|---|---|---|---|---|
| | % IFNγ+ amoung CD8 cells | | | % IFNγ+ amoung CD8 cells | | |
| | Day 0 | Day 14 | Day 28 | Day 0 | Day 14 | Day 28 |
| n | 6 | 6 | 6 | 4 | 4 | 4 |
| Median | 0.00 | 0.06 | 0.00 | 0 | 0 | 0 |
| IQR | 0.15 | 0.19 | 0.17 | | | |
| positive responses | 1/6 | 4/6 | 2/6 | 0/4 | 0/4 | 0/4 |
| Non-parametric Mann-Withney test | | ns | | | ns | |

VACCINATION BY TRANSCUTANEOUS TARGETING

Cross-Reference to Related Applications

The present application is a 35 U.S.C. §371 National Stage patent application of International patent application PCT/IB2006/002417, filed on Jun. 23, 2006, which claims priority to French patent application FR 05/06412, filed on Jun. 23, 2005.

The present invention relates to a method of vaccination via the hair follicles that makes it possible to target vaccine components to the antigen-presenting cells in order to induce a protective and effective immune response against pathogens.

Vaccination is an effective means of preventing or reducing viral or bacterial infections. The success of vaccination campaigns in these fields have made it possible to extend the vaccine concept, up until now used in the infectology field, to the fields of cancer and autoimmune diseases.

Vaccination via "conventional" routes: intramuscular, intradermal in solution, has many constraints when put into practice. Conventional vaccination techniques in fact have the disadvantages of requiring the use of needles and, by the same token, of causing sterility and wound problems, and are also problematic in terms of instability of the vaccines after reconstitution in solution and in the case of non-observance of the cold chain during the storage and transport thereof.

Furthermore, the vaccine preparation must subsequently then reach the secondary lymphoid organs which are the sites of the immune response. During the vaccine preparation's path to these organs, the antigen of the preparation can be diluted in the body fluids, trapped in tissues that are not competent for the expected immune response, or degraded, which leads to a considerable loss of the vaccine preparation initially injected. Consequently, the amounts of vaccines injected must be substantial in order to compensate for these losses.

The skin is an organ particularly rich in antigen-presenting cells, these cells absolutely necessary for the induction of potent and effective vaccine responses. Their location and their function are particularly well studied and known.

It has in fact been known for a long time that an effective and strong immune response can be induced subsequent to degradation of the skin barrier, such as scarification in the case of smallpox in humans, for example. However, studies show that vaccination with naked plasmid DNA encoding a hepatitis B surface antigen in aqueous solution on intact mouse skin also produces specific and strong immune responses (Fan 1999).

It has recently been shown that it is possible to induce immune responses in mice following topical applications of vaccines to the skin of these animals, freed beforehand of keratinocytes (Ishii N, et al., (2001) *J. Investig. Dermatol. Symp. Proc.* Nov 6(1) pp 76-80). Similarly, it has been possible to induce a response to HIV virus DNA in monkeys infected with this virus (Lisziewicz J., et al. 9th conference on Retroviruses and Opportunistic Infections. Seattle, February 2002). Studies have been carried out following the vaccination of monkeys with 0.1 μm-diameter particles consisting of polyethyleneimine and mannose coated with DNA. A surface area of at least 40 cm$^2$ of the monkeys' skin was necessary to carry out this experiment. A crude estimation evaluates at 1% the number of Langerhans cells (antigen-presenting cells) expressing the DNA introduced (Derma-vir) (Lisziewicz, J., et al., (2005) *J. Invest. Dermatol., January* 124(1), pp 160-9).

These studies thus demonstrated that transcutaneous vaccination in animal models makes it possible to induce an effective immune response. The transcutaneous vaccination methods available to date involve, however, vaccine preparation procedures which are often complex, and a method of administration which is most commonly invasive (shaving, scarification, abrasion of upper layers of the epidermis, etc.) associated with the use of a large surface area of the patient's skin. Furthermore, the risk of loss of the product via the bloodstream is absolutely not taken into account.

The percutaneous absorption of compounds applied to intact skin is in fact limited by the stratum corneum, which forms a very structured barrier at the surface of the skin, which explains the need up until now to alter this stratum corneum by physical methods. The passage of molecules through the cornified layer of the skin takes place at a very low diffusion rate and the largest molecules, of which proteins are a part, succeed in crossing this barrier only with great difficulty.

It is, however, known from Patents U.S. Pat. Nos. 5,910,306 and 5,980,898 (US Army) that an approach by transcutaneous application of vaccine can also be applied to humans. In fact, the authors of U.S. Pat. No. 5,980,898 have, for example, inducted a strong immune response following transcutaneous immunization of a labile enterotoxin of the *E. coli* bacterium using a patch system. However, the drawback of this approach is that it requires the application of the vaccine preparation over a large surface area of the individual's skin.

Under physiological conditions, the concentrations of active products applied topically are low, particularly if they are formulated in the form of dilute pharmaceutical preparations. This is due in part to the fact that conventional preparations of active compounds in solution disperse at the surface of the skin, which results in low local concentrations of active compound. In addition, the lower the effective local concentration, the greater the risks of these active compounds binding to proteins of the skin nonspecifically, which reduces even further the free concentration available for vaccination.

Most of all, since the epidermis is continually being renewed, the bound active compounds are inevitably lost during this renewal.

The elements of the skin however, and in particular the hair follicles, are sites of discontinuity that are important in the barrier function of the skin.

Various studies have shown that the hair follicles are, despite their small size compared with that of the epidermis between two follicles, a predominant route of access for percutaneous absorption of foreign material, including active compounds (Hueber 1994, Tenjarla 1999). Furthermore, the insertion of hair follicles into a modified skin increases the rate of penetration of hydrocortisone (Michel 1999).

The Applicant has developed a method of vaccination via the hair follicles that makes it possible to target components of the vaccine preparation to the antigen-presenting cells in order to induce a protective and effective immune response against the pathogens.

The Applicant has thus discovered that this method of targeted vaccination makes it possible to make accessible to the vaccines the professional antigen-presenting cells located around the hair follicles. A subject of the invention is thus a method of targeted vaccination and also the preferential access of the components of the vaccine preparation to the antigen-presenting cells.

The targeting of the vaccination results in high concentrations of vaccine preparation in the hair follicle, in proximity to the antigen-presenting cells present in the follicle, which cells, unlike those of the interfollicular space, are very accessible to active compounds applied topically.

The Applicant has thus discovered the therapeutic or preventive use of a vaccine optimized by specialization of the route of transcutaneous entry of the vaccine preparation and targeting of the antigen-presenting cells of the skin (dermis and epidermis) making it possible to reduce the surface area of inoculation of the vaccine.

A subject of the invention is thus the use, for a vaccine preparation, of particles of a given size. Specifically, after possible deformation, these particles exhibit at least a cross section having a diameter of between 0.1 nm and 0.2 µm.

Another subject of the invention is the use of such particles for preparing a therapeutic vaccine composition.

Another subject of the invention is the use of such particles for preparing a therapeutic or prophylactic vaccine composition useful in immunosuppressed individuals.

Other subjects of the invention will become apparent in the light of the description, of the examples which follow and of the drawings attached in the annex to the present application.

FIG. 1 shows the disorganized penetration of the particles in the case of destruction of the epidermal layer due to repeated applications of glue. The two figures at the top show the fluorescent particles after one application of glue (arrow). The two figures at the bottom show the entry of fluorescent particles after three applications of glue.

Figure 4:
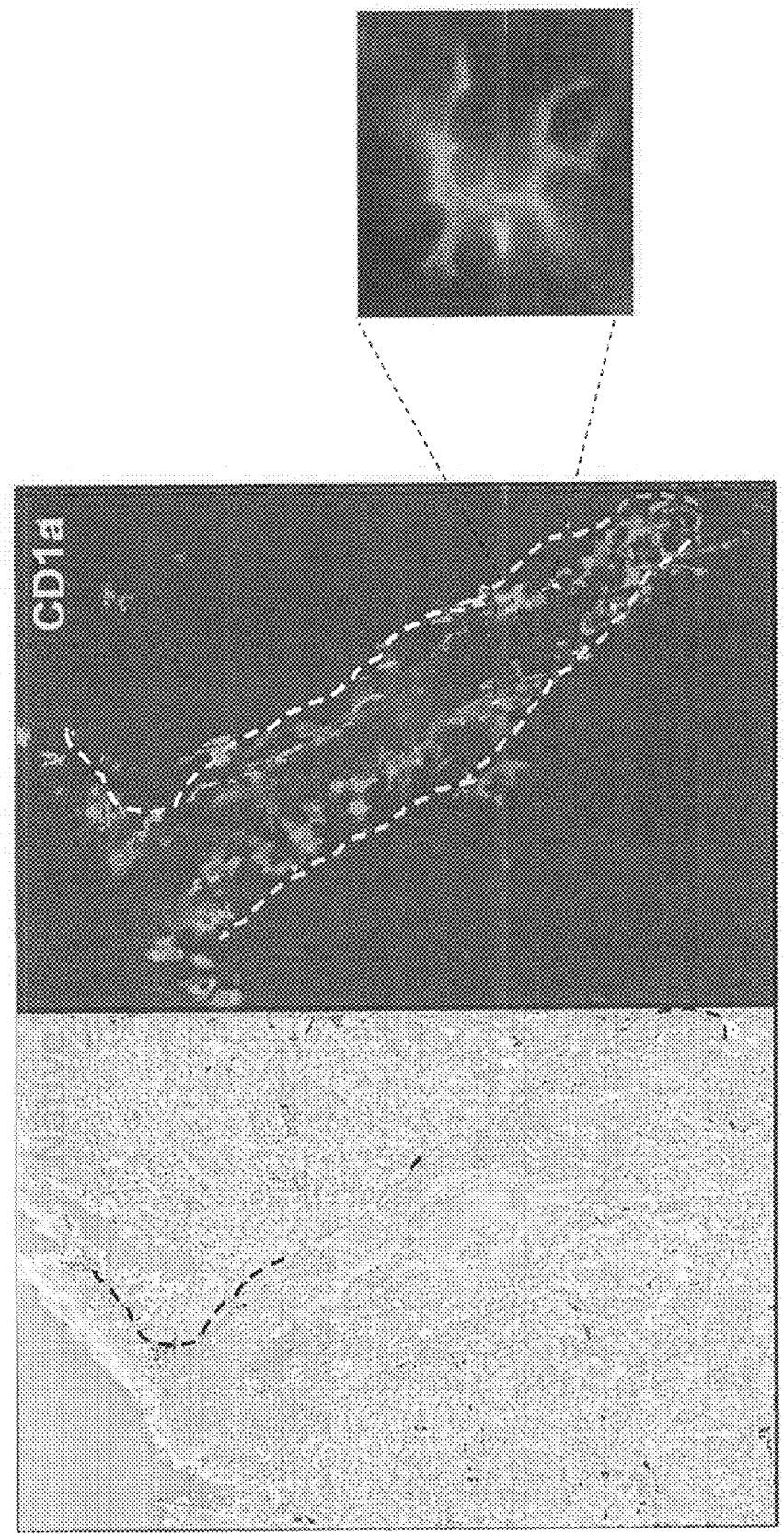

FIG. 4 demonstrates, using fluorescence, the specific expression of the Langerhans cell marker CD1a around the hair follicles. The enlargement shows a Langerhans cell labelled by fluorescence.

Figure 5:
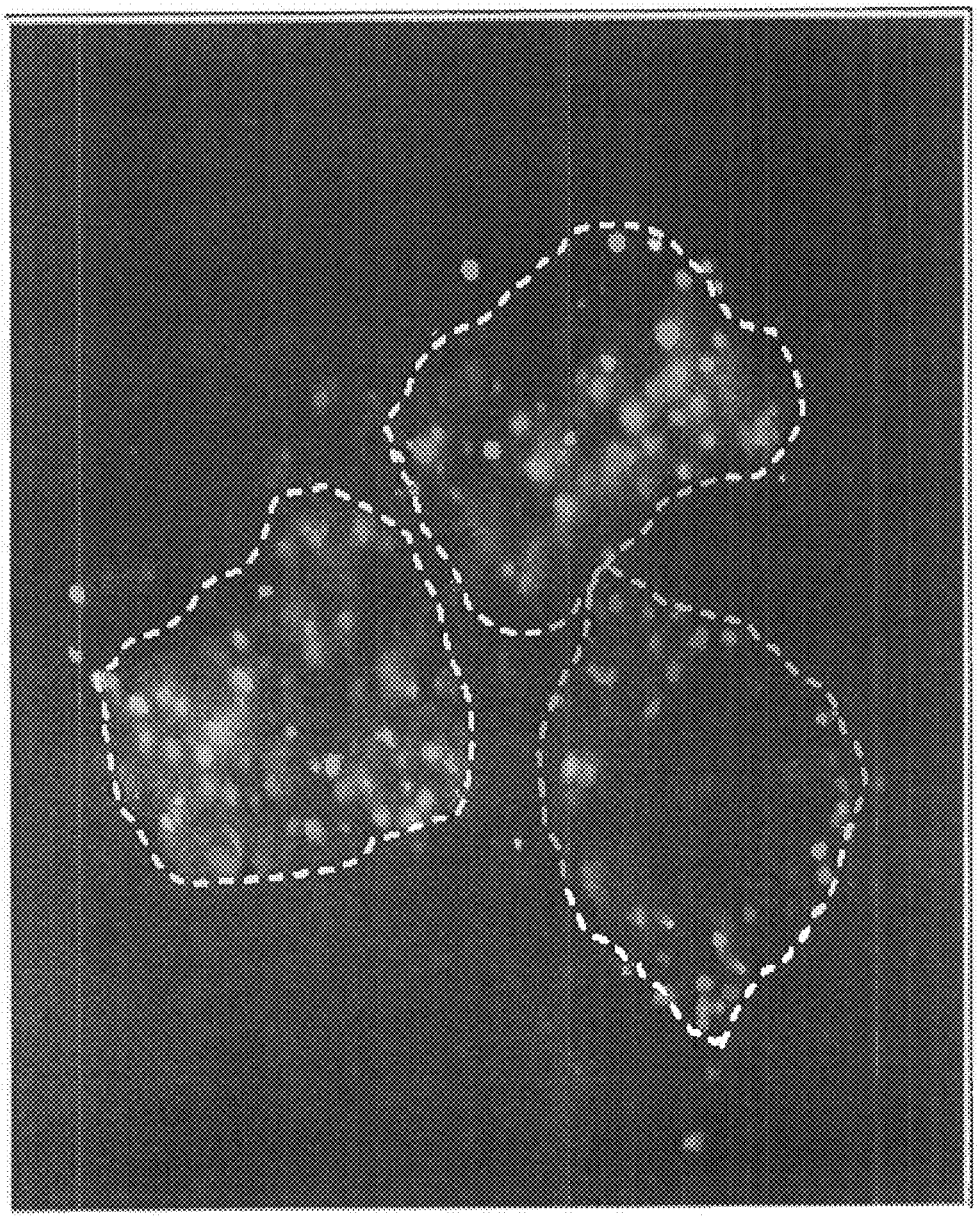

FIG. 5 shows the penetration of the fluorescent particles in the Langerhans cells after transcutaneous application at 37° C. The dashed lines represent the outlines of the Langerhans cells.

Figure 6:
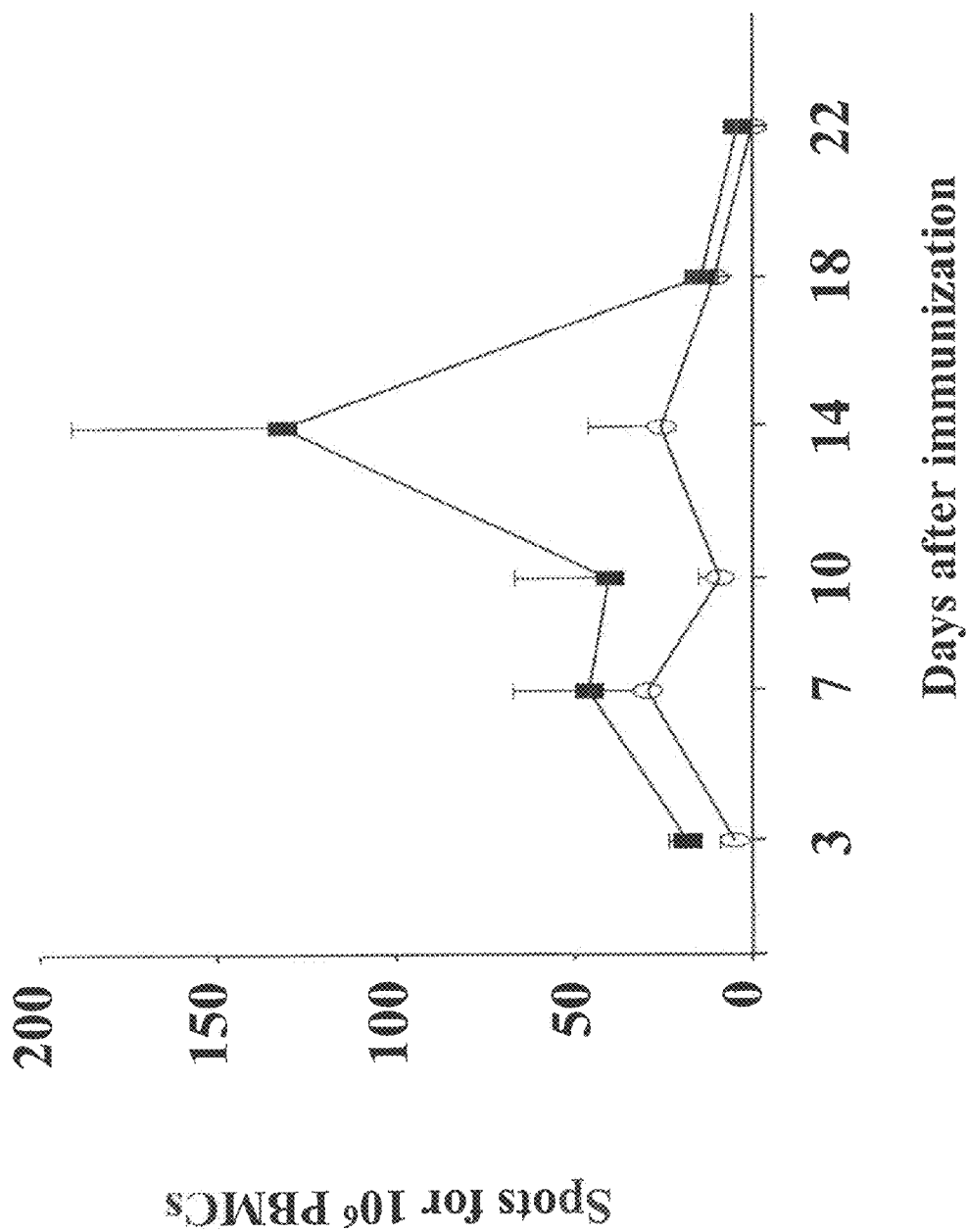

FIG. 6 shows the measurement of the specific immune T response with the TETAGRIP® vaccine (Aventis Pasteur) in a murine model of transcutaneous vaccination. The antigen-specific cell responses induced by the vaccination are determined ex vivo by the EliSpot technique using peripheral blood cells at various times post-vaccination. The black squares represent the effective immune T responses after transcutaneous immunization with the TETAGRIP® human vaccine (n=11) and the open circles represent the negative control (n=6).

Figure 7:
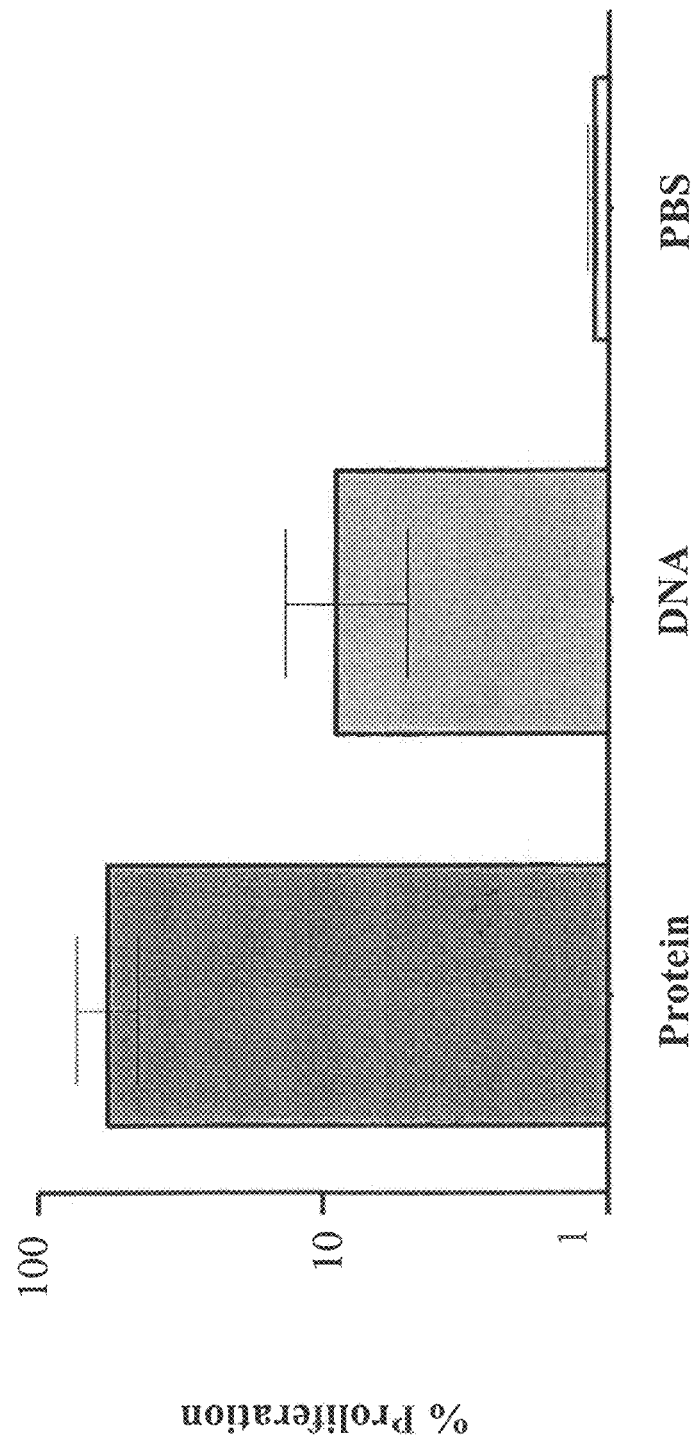

FIG. 7 shows the measurement of the specific proliferative T response with the TETAGRIP vaccine in a murine model of transcutaneous vaccination.

Figure 8:
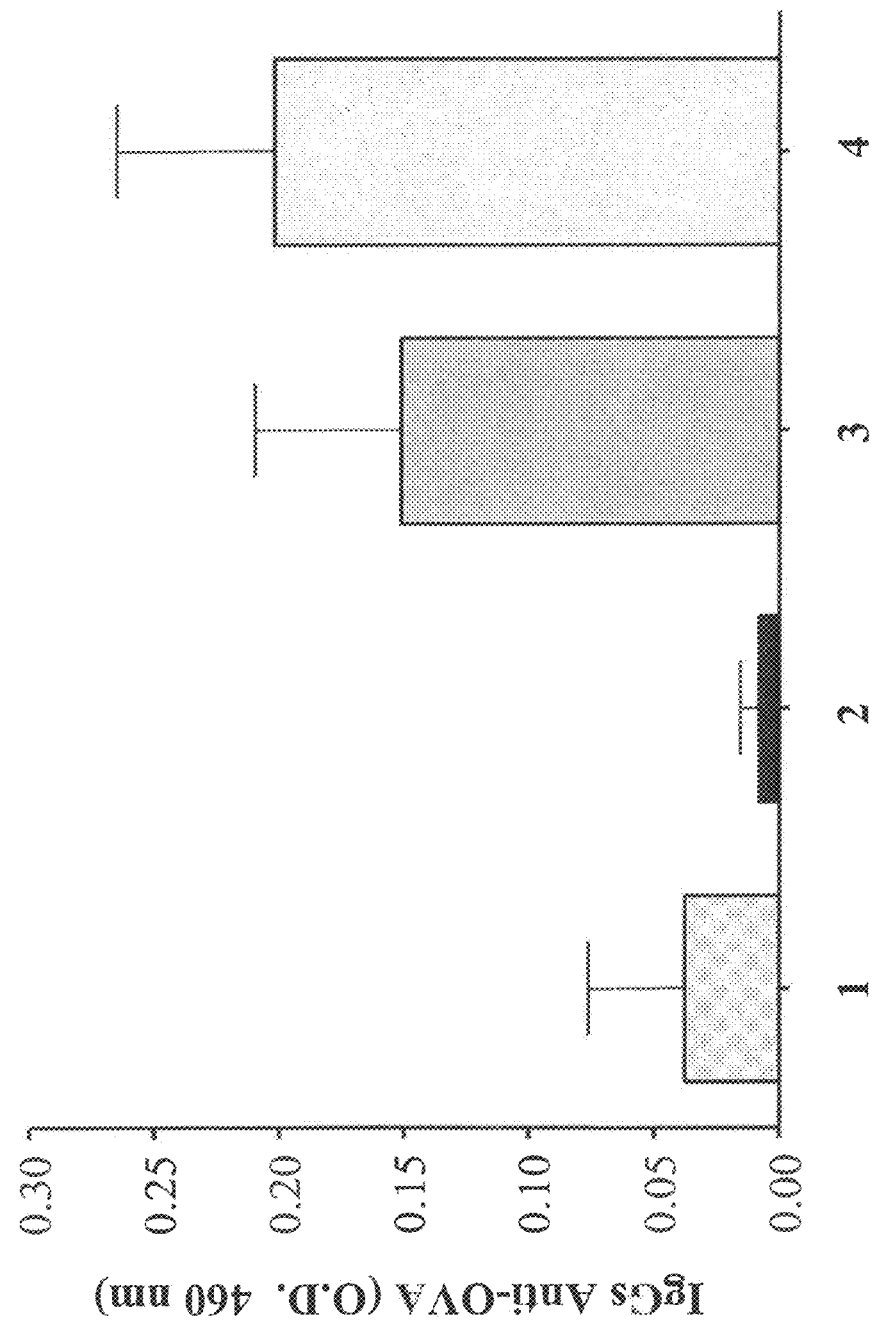

FIG. 8 shows the measurement of the specific humoral response with the TETAGRIP vaccine in a murine model of transcutaneous vaccination. The No. 1 corresponds to a control administration of PBS (n=5), the No. 2 corresponds to the OVA protein (n=6), the No. 3 corresponds to the OVA protein with FITC-labelled cholera toxin (n=7), and No. 4 corresponds to OVA plasmid DNA.

Figure 9A:
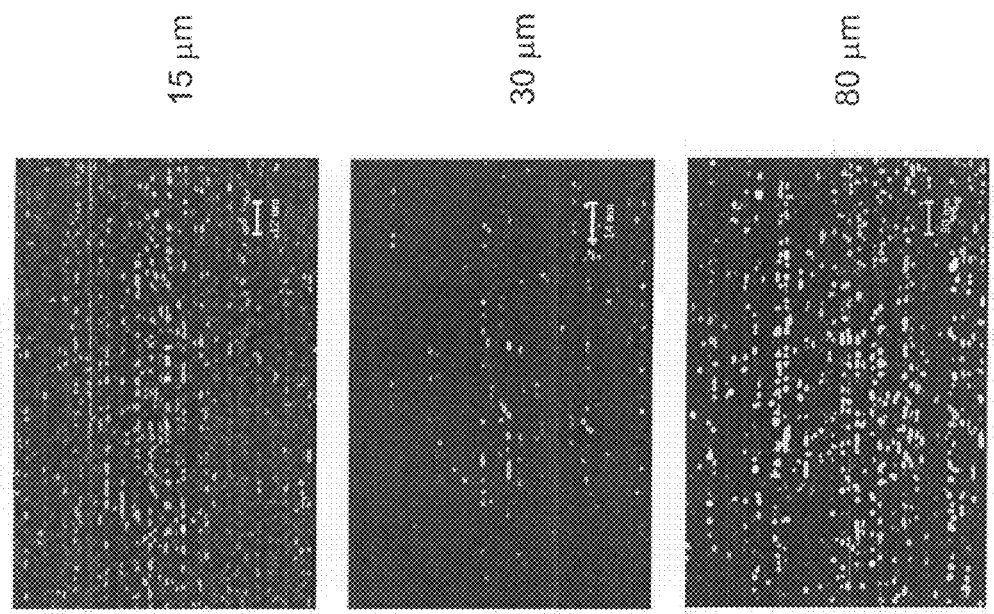

FIG. 9A shows the location of the fluorescent particles in a model of transcutaneous vaccination at various depths 5 hours after immunization.

Figure 9B:
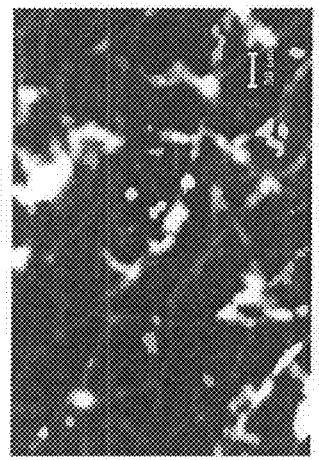
Figure 9B:
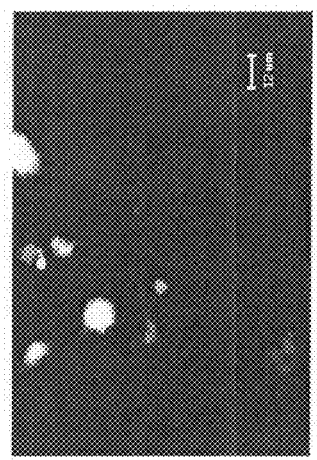
Figure 9B:
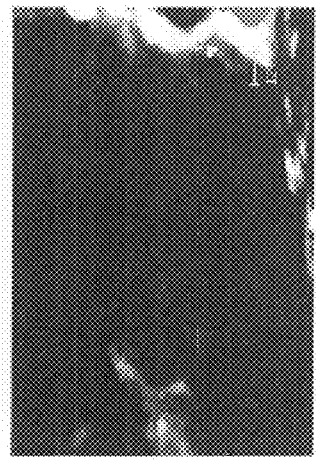

FIG. 9B is the negative control at various depths in the absence of particles 5 hours after immunization.

Figure 10B:
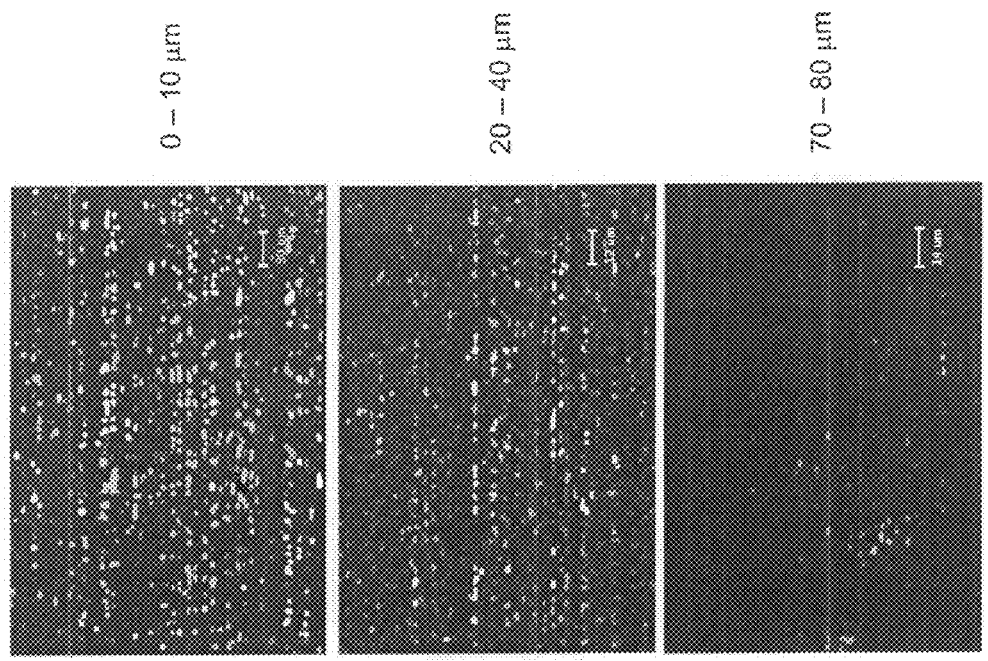
Figure 10A:
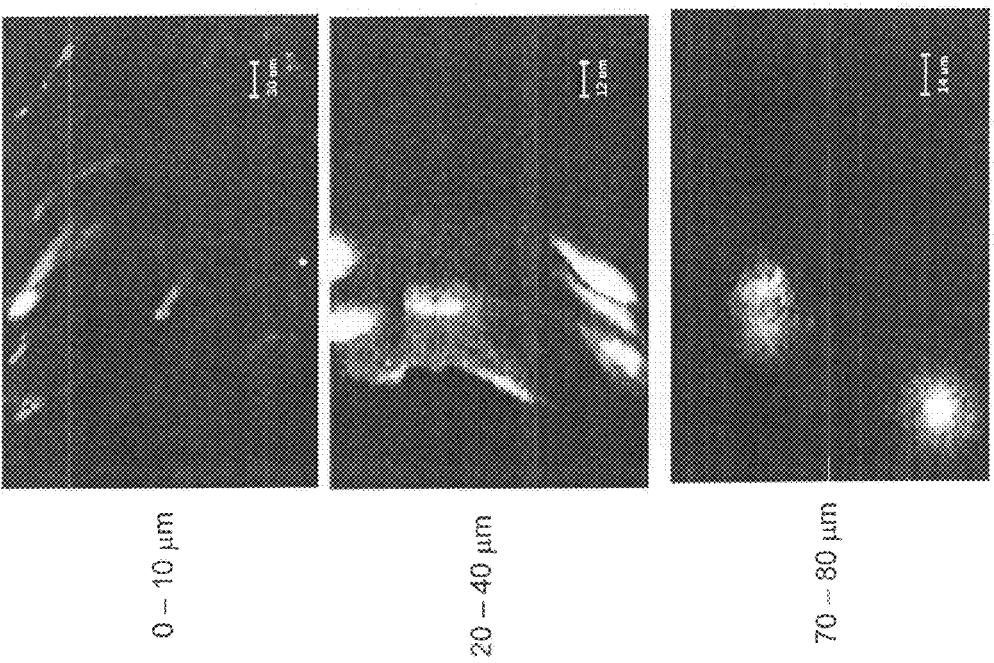

FIG. 10A shows the location of the fluorescent particles in a model of transcutaneous vaccination using a probe for observing the fluorescence at various depths 24 hours after immunization and the diffusion of this fluorescence in the area around the hair follicle.

FIG. 10B is the negative control with a probe for observation at various depths in the absence of particles 24 hours after immunization.

Figure 11C:
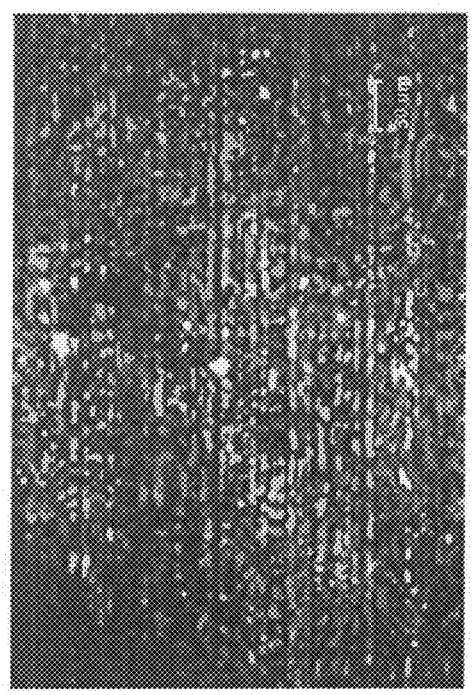
Figure 11A:
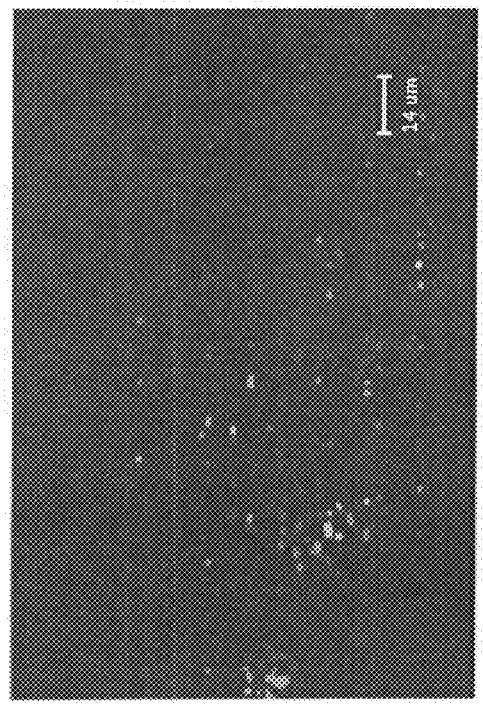
Figure 11B:
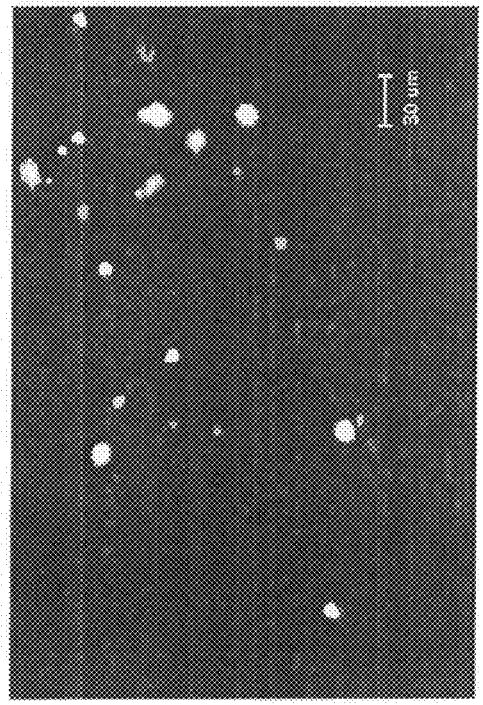

FIG. 11 shows the location of the particles in the lymph nodes following transcutaneous vaccination. A: control node, B: inguinal node, C: axial node.

Figure 12:
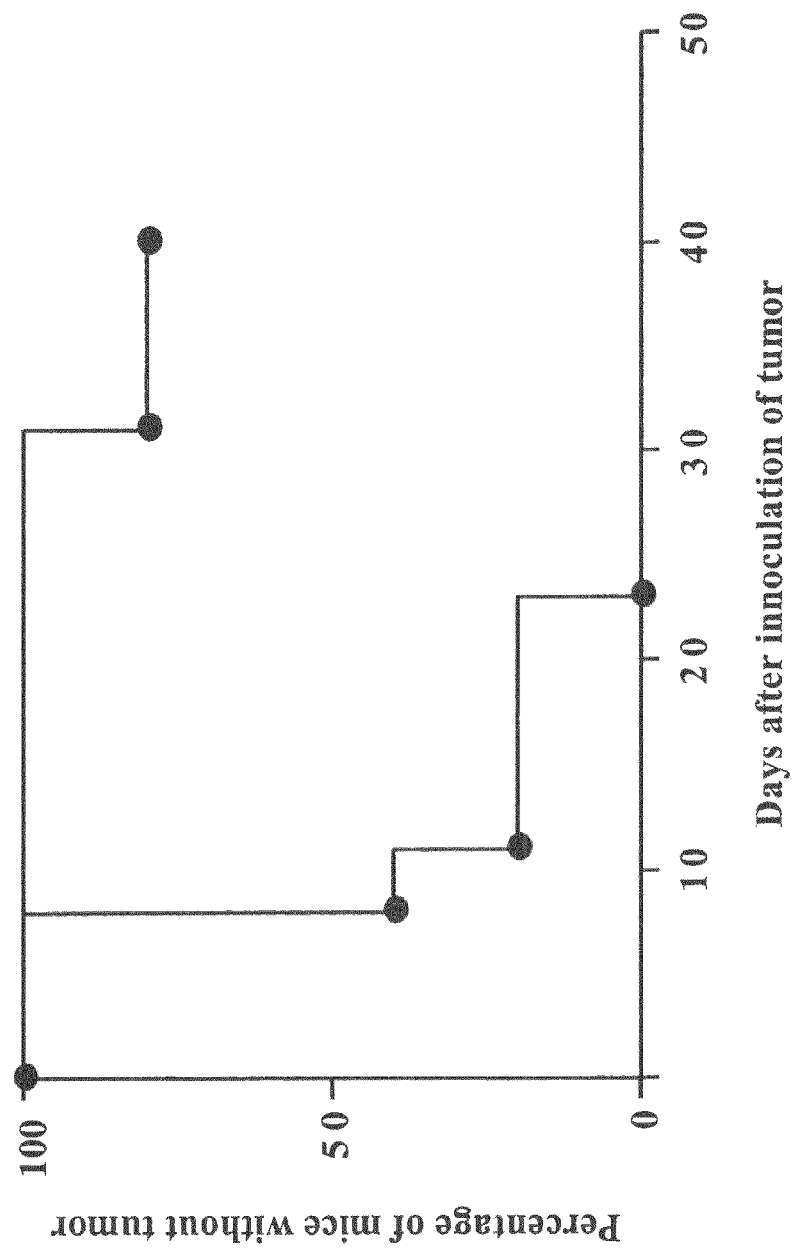

FIG. 12 shows the measurement of the specific protective T response with the TETAGRIP vaccine in a murine model of transcutaneous vaccination as a function of time. The open circles symbolize the mice having received the EL-4 cells without antigen (n=4) and the black circles symbolize the mice having been vaccinated with the EG-7 cells (n=4).

FIG. 13 shows the frequencies of the influenza-specific effector T lymphocytes. The Elispot assays were carried out on peripheral blood samples at days 0, 14 and 28. The effector T cell response is measured by the IFNγ-ELISPOT technique and compared between transcutaneous and intramuscular groups using Mann-Witney test ns=not significant p value>0.05 (Mann-Witney test). IQR=inter quartile range.

Figure 14B:
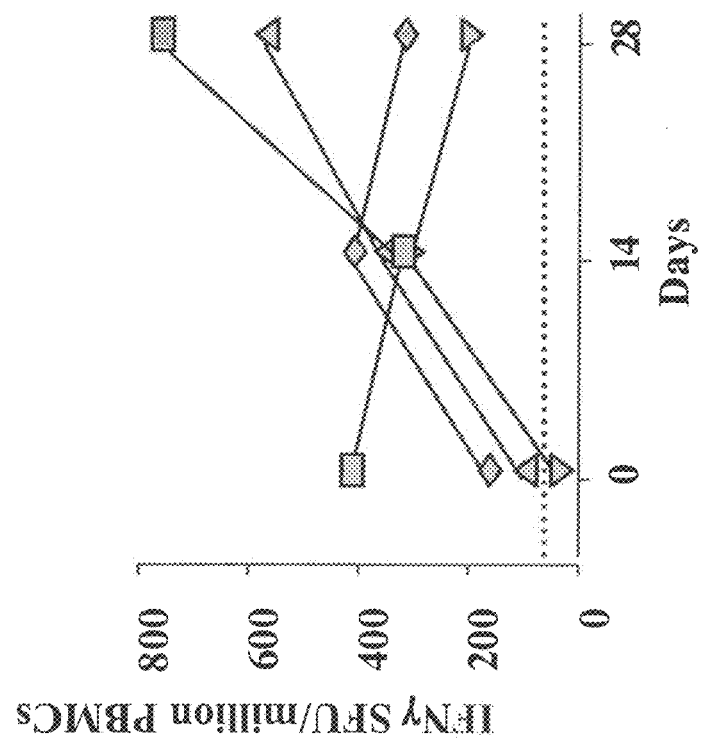
Figure 14A:
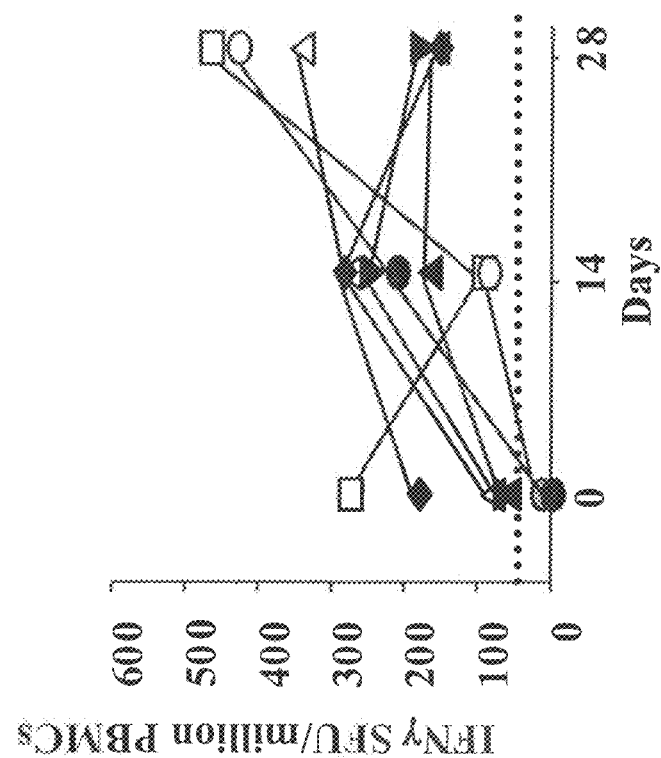

FIG. 14A shows the response of the effector T cells following transcutaneous immunization. The solid symbols represent a surface area of 16 $cm^2$; the circles symbolize volunteer 1, the upward-pointing triangles symbolize volunteer 4, the downward-pointing triangles symbolize volunteer 6 and the diamonds symbolize volunteer 7. The open symbols represent an application surface area of 32 $cm^2$. The continuous lines symbolize volunteer 2, the rectangles symbolize volunteer 3 and the triangles symbolize volunteer 5.

FIG. 14B represents the response of the effector T cells following immunization with an intramuscular injection. The shaded squares represent volunteer 8, the upward-pointing triangles represent volunteer 9, the downward-pointing triangles represent volunteer 10 and the diamonds represent volunteer 11. The effector T cell response is measured by the IFNγ-ELISPOT technique.

FIGS. 15A and 15B represent respective frequencies of Influenza-specific effector T lymphocytes by ELISPOT assay following transcutaneous or intramuscular administration (FIG. 15A, CD4 T cells, FIG. 15B, CD8 T cells). The evolution between day 14 and baseline (or day 28 and baseline) were compared between transcutaneous and intramuscular groups using Mann-Witney test ns=not significant p value>0.05 (Mann-Witney test).

Figure 16:

FIG. 16 represents the intracytoplasmic IFNγ-production by flow-cytometric assay in CD4 and CD8 T cells after 16 h stimulation with the Aggripal® vaccine (1/1000 dilution). Results are representative of either influenza-specific CD4 or CD8 producing IFNγ at different time points after transcutaneous vaccination.

The use of this vaccine preparation according to the invention comprises the following steps:
a) Pretreatment of the skin in order to improve the opening of the hair follicles by ablation of at most 50% of the corneal layer.
b) The use, for preparing this vaccine preparation, of particles which, after possible deformation, exhibit at least a cross section having a diameter of less than or equal to 0.2 µm.
c) The specific entry of this vaccine preparation via the hair follicles, the small size of the particles allowing their diffusion through the epithelium of the hair follicle.
d) Induction, stimulation or augmentation of the protective immune and cellular responses.

The targeting of the active compounds directly to the heart of the hair follicles is carried out by means of particles of a given size. It was in fact known that beads having a size of the order of 3 to 10 µm applied topically to human skin aggregate at the level of the follicular orifices, whereas beads having a size greater than 10 μm remain at the surface of the skin (Rolland 1993).

However, beads or crystals having a size of up to a few micrometers can in fact be introduced into the follicular duct.

Thus, although solutions spread out at the surface of the skin nonspecifically, Toll and his team have shown that beads aggregate in the follicular orifices as a function of their size. Specifically, they observed a preferential penetration of particles having a size of 1.5 to 6 μm in diameter in the follicular duct of hair follicles from human scalp, but particles of these sizes do not, however, penetrate into the epithelium (Vogt, unpublished results).

However, smaller particles, of the order of 0.2 μm in diameter, penetrate, on the other hand, deeply into the hair follicles. Particles of this size can contain or be coated with antigens, for example. These particles are then capable of penetrating into the epidermal Langerhans cells under normal physiological conditions and allowing delivery of the vaccine preparation directly in contact with the cells concerned.

Langerhans cells, which are epidermal immature dendritic cells, constitute, with the dendritic cells located in the dermis, a reservoir of immune system sentinel cells (Kupper T., et al., (2004), *Nat. Rev. Immunol.* 4(3) pp 211-222). They are closely involved in the immune response via the transcutaneous route. Following their activation, they will subsequently migrate to the draining lymph nodes and contribute to the immune response. Langerhans cells are concentrated around the hair follicle in humans. This property makes Langerhans cells targets of choice for the cutaneous administration of antigenic preparations.

The particles according to the invention are thus particles which, after possible deformation, exhibit at least a cross section having a diameter of between 0.1 nm and 0.2 μm. It is also possible to use solid particles whose diameter is between 0.1 nm and 0.2 μm. Alternatively, particles which can deform until a cross section having a diameter of between 0.1 nm and 0.2 μm is created are also included in the invention, such as, for example, viral particles.

Preferably, the particles according to the invention exhibit, after possible deformation, at least a cross section having a diameter of between 0.1 nm and 0.1 μm. More preferably, these particles exhibit, after possible deformation, at least a cross section having a diameter of between 0.1 nm and 0.05 μm.

Contrary to the methods described above, the targeting of the components of the vaccine preparation to the hair follicles makes it possible to apply the components of this vaccine preparation over a smaller surface area (less than 20 $cm^2$) of the skin. The components of the vaccine preparation penetrate specifically, by virtue of their size, via the hair follicles and target essentially the antigen-presenting cells which are essential in the induction of an immune response.

The use according to the invention thus comprises the prior step of pretreatment, i.e. of opening, of the hair follicles by carrying out an ablation of at most 50% of the corneal layer.

This step can be carried out using adhesive strips or "tape stripping". In fact, on hairless skin, about a third of the hair follicles are open under normal conditions. In order to improve the targeted entry of the vaccine preparation, adhesive strips are used, such as those of the TESA trade mark which are not aggressive for the skin, allowing opening of the hair follicles and removal of the dead cells of the upper corneal layer (at most 50%) of the skin while at the same time conserving the integrity of the skin at the epidermal and dermal level.

It has been demonstrated that tape stripping per se induces activation of antigen-presenting cells and the maintenance of a pool of Langerhans cells around the hair follicles (J Exp Med 1982).

Alternatively, treatment with adhesive or glue can be carried out. This consists in applying to the skin a few drops of instantaneous adhesive (cyanoacrylate-based glue), applying a covering material (adhesive strip, cloth, etc.) by pressing and removing it after a few minutes. This action removes the upper part of the closed follicle. This treatment thus makes it possible to remove 30% of the thickness of the corneal layer at each application of glue. It is thus possible to remove up to 50% of the thickness of the corneal layer without affecting the specificity of entry of the particles into the hair follicle.

The particles according to the invention contain the antigen, i.e. they can comprise or be coated with antigen. It is understood that the particles according to the invention are coated with antigen or encapsulated by known means of adsorption and lyophilization so as not to exceed, at least for one cross section, a diameter of 0.2 μm for possibly deformable particles.

The term "antigen" is intended to mean proteins, glycoproteins, peptides or peptide fractions, polysaccharides, polyosides, lipopolysaccharides, toxoids, conjugated carrier proteins, cell extracts, viral extracts, bacterial extracts, parasitic extracts, live, attenuated, killed, inactivated or recombinant viral, bacterial or parasitic particles, viral pseudoparticles, DNA, polynucleotides, recombinant nucleic acids of pathogens, molecules involved in orphan diseases and cancers, cancer cell extracts. The term "antigen" is also intended to mean fragments of whole proteins on condition that these fragments have at least one immunogenic epitope determinant.

The amount of antigen in a dose of vaccine preparation is the amount which induces a protective immune response without side effect. Such amounts vary according to the antigen used and can be determined by conventional studies including observation of the antibody titres obtained in the individuals vaccinated. Typically, the doses in a human are from 0.1 to 1000 μg for an antigen in the form of a nucleic acid.

Alternatively, the vaccine preparation can be incorporated into particles of wax having a melting point of 37 to 40° C., and the particles or beads having a diameter of between 0.1 nm and 0.2 μm are thus formed by methods known to those skilled in the art. Aqueous preparations of these wax beads are prepared by means known to those skilled in the art. These wax particles can be applied to the skin of the individual to be vaccinated. Once inside the hair follicle, they will melt in response to the heat thereof, releasing the vaccine preparation in situ.

Alternatively the particles may be liposomes, lipopeptides, virosomes or glycoliposomes including phospholiposomes.

Use may also be made of polymeric nanoparticles either coated with or encapsulating the vaccine antigens and based on the polymerization of polyesters, for instance poly(lactic-co-glycolic acid) (PLGA), polylactic acid (PLA) or polyethyleneimine (PEI). The use of nanoparticles comprising nanoparticles of polylactic acid loaded with peptides and/or proteins and/or DNA and/or nucleic acid is also included in the invention.

Microsponges of appropriate size are also included in the particles according to the invention. Preferably, these microsponges are of a heat-absorbing colour. These microsponges are loaded with the vaccine preparations by saturation, before lyophilizing them. The loaded microsponges are subsequently resuspended in appropriate oil and applied to the skin of the patient to be treated. Thus, because of their small size, these microsponges loaded with vaccine preparation penetrate deeply into the follicular duct. Appropriate microsponges are, for example, those sold by Cardinal Health Pharmaceutical Technologies & Services, Somerset, N.J., USA.

Dispersions of charcoal, of titanium dioxide, of zinc oxide, of iron oxides and of talc of an appropriate size can also be envisaged. Once loaded with the vaccine preparation, these particles are prepared in nonaqueous transporters such as oil and used in the same manner as the microsponges. Any cosmetic or pharmaceutical hydrophobic oil, preferably among the oils of the pharmacopoeia, can be used.

The particles according to the invention can also comprise or consist of naked DNA encoding a part of the HIV genome.

The particles according to the invention also include possibly deformable viral particles. Preferably, the viral particles are inactivated HIV particles which may or may not be recombinant. These particles can also be viral particles of attenuated poxviruses.

It is possible, in order to accelerate the release of the vaccine preparation and facilitate its diffusion in contact with the Langerhans cells, to moderately heat the area of skin to be treated, for example by means of a red or infrared lamp, of a microwave-emitting apparatus or a similar device, etc.

It is possible to add, to the vaccine preparation to be administered, adjuvants in the form, for example, of an oily emulsion or of a fatty substance such as vaseline, of cytokines, of chimokines, of growth factors, of pathogen derivatives, of lipids, of polysaccharides, of polypeptides, of lipopolysaccharides, of oligosaccharides, of copolymers, of PAMs (pathogen-associated molecular patterns), of "toll-like receptor" ligands, of MPL-A (monophosphoryl lipid A), of Quil-A, of ISCOM, of Dimethyl Dioctadecyl ammonium bromide (DDAB) or Dimethyl Dioctadecyl ammonium chloride (DDAC), of CpG motifs, of Leif, of toxoids, for instance cholera toxin (CT), LT (Heat Labile Toxin) and detoxified versions of CT or LT, etc. All the other "adjuvant"-type molecules described in the literature can also be used for this route of immunization.

These adjuvants are products which increase the reactions of the immune system of humans when they are administered in the presence of the antigen. They increase the production of specific immunoglobulins, antibodies, and stimulate numerous cells involved in the immune defence mechanisms.

These particles which, after possible deformation, exhibit a cross section having a diameter of between 0.1 nm and 0.2 μm can be placed in an appropriate carrier, for example petroleum jelly, which does not dissolve the vaccine preparation and which can be applied to the skin, preferably to the cheek or to the lower back of the human to be vaccinated. Once deposited at the surface of the skin, prepared beforehand, the particles will go into the hair follicles, in a targeted manner due to their small diameter. The vaccine preparation will then dissolve in place by means of the interstitial fluid, providing the vaccine at a high concentration, in situ.

The particles according to the invention are thus useful for preparing a therapeutic vaccine composition comprising them. The vaccine composition is intended to be used in humans in whom it may be for curative or preventive purposes. This therapeutic vaccine composition is useful for targeting, through the hair follicles, the vaccine components of the vaccine preparation to the antigen-presenting cells. Once prepared, this vaccine composition has the advantage of being thermostable, which makes it readily usable under difficult climatic conditions.

The use according to the invention thus allows targeting of the components of the vaccine preparation to the hair follicles and, as a result, to a very large number of antigen-presenting cells of the dermis and of the epidermis. This specific method of administration allows rapid uptake of the vaccine components by the targeted cells (Langerhans cells and dendritic cells) and also the capture and the expression of the vaccine components by the antigen-presenting cells and activation of these cells. A main reservoir of antigen located in the professional antigen-presenting cells is therefore maintained.

By virtue of the specificity of the targeting, a high concentration of antigens is obtained in a reduced surface area of application of the vaccine to the patient's skin.

Next, the antigen-presenting cells migrate to the secondary lymphoid organs and the induction of a humoral and cellular immune response is observed. This will thus allow the establishment of long-term protective immunity after the vaccination.

It may be recalled that the immune response is relayed by the lymphocytic cells, in particular the B cells and the T lymphocytes. The latter can be classified as two subtypes on the basis, inter alia, of their CD4 and CD8 surface antigen expression. CD4 T cells are generally involved in "helper" functions. In particular, they secrete cytokines which induce the proliferation and maturation of the other lymphocytic cells. CD8 T cells, which are predominantly expressed compared with CD4 T cells, correspond to the cells involved in a cytotoxic cellular immune response referred to as being of CTL type.

In particular, a direct cytotoxic activity has been described for certain CD4+ T lymphocytes. Two types of effector immune response exist: the humoral response due to antibodies and the cytotoxic response due mainly to CD8 T lymphocytes. An effective cytotoxic response requires presentation of the antigens to the CD8+ cytotoxic T lymphocytes (CTLs) in association with the major histocompatibility complex MHC class I molecules, but also to the CD4+ helper T lymphocytes in association with the MHC class II molecules.

Although mucosal and systemic antibodies are considered to play a major role in the prevention of certain infections, the induction of cell-mediated immunity, including the induction of a cytotoxic T lymphocyte (CTL) response, is particularly necessary for combating intracellular pathogens (viruses, bacteria or parasites) and for controlling tumour processes. The induction and the regulation of CTLs are dependent on the cytokines (IL-2, etc.) produced by the Th1 subpopulation of CD4 helper cells. The cytotoxic T lymphocytes (CTLs) play an essential role in the "clearance" of intracellular pathogens and also in the control of tumours. The CD8 T lymphocytes recognize the peptide fragments, derived from intracellular degradation of the antigen, in the form of a complex with the MHC class I molecules expressed at the surface of the cell. This recognition leads to lysis of the cells carrying the MHC-antigenic peptide complex. The CTLs also generate various lymphokines (IFNγ and TNFα) which can, as a supplement, be directly cytolytic. The induction of CTLs is therefore considered to be an essential component of vaccines designed for the prevention and treatment of these diseases. Among the treatments currently proposed for combating cancers and chronic viral infections, vaccination is becoming an increasingly important component. The aim of therapeutic vaccination is to induce or to restimulate in vivo a specific immune response capable of destroying infected cells or tumour cells. The immune response of the patients must be modulated such that it becomes effective and induces a cell-mediated response specific for antigens expressed, for example, by the tumour and capable of eliminating the cancer cells.

The transcutaneous use of this vaccine preparation induces all cellular (CD4, CD8, etc.) and humoral (antibody production, B cell responses, etc.) immune responses in humans. Thus, the transcutaneous vaccination is applicable to vaccines of any type and makes it possible to induce a protective immune response against the vaccine by targeting the vaccine directly to the professional antigen-presenting cells.

Moreover, the immune response induced by transcutaneous vaccination may differ qualitatively from the immune response obtained by conventional intramuscular injection. Indeed, CD8 positive cells can be found after transcutaneous vaccination in human volunteers, while no detectable CD8 cells were found after intramuscular vaccination. In a specific embodiment, the transcutaneous use of this vaccine allows the induction of CD8 T cells immune response.

This route of administration could also be interesting in immunosuppressed individuals. Indeed, these individuals respond poorly to the majority of vaccines administered through a conventional route (intramuscular, subcutaneous of intradermically)

When injected via intramuscular route in healthy individuals, the conventional live attenuated vaccines easily induce strong CD8 T cells that are essential for the control of many pathogens (mostly viruses) and tumors. However, these vaccines (such as against tuberculosis, measles, mumps, rubeola, varicella, yellow fever, variola . . . ) are contra-indicated in all immunosuppressed individuals, both chronically and transiently immune-suppressed such as during pregnancy, because of the risk of uncontrolled dissemination of the live attenuated pathogen in immunosuppressed individuals. In contrast, inert or inactivated non replicating vaccines which are allowed in such immunosuppressed individuals cannot induce CD8 T cell responses. Therefore immunosuppressed individuals cannot be protected against the diseases mentioned above or others requiring CD8 T cell responses.

On the contrary, a transcutaneous administration of an inert or inactivated vaccine preparation allows the direct targeting of the skin dendritic cells surrounding the hair follicles, the improved in vivo loading of vaccine antigens into these dendritic cells and the cross-presentation of exogenous inert antigens through the HLA-class I molecules to the CD8 T lymphocytes, by these targeted dendritic cells once they reach the draining lymph nodes All groups of immunosuppressed individuals benefit from the process:
  HIV-infected patients
  Transplanted recipients
  Patients on immunosuppressive, chemotherapy regimens, or irradiated patients,
  Patients with any kind of acquired or congenital or inherited immune deficiencies (such as SCID [Severe Combined Immunodeficiency], DiGeorge syndrome . . . ). . .
  Pregnancy (due to the transient immunosuppression observed during pregnancy) which imposes another contra-indication to live vaccines due to the risk of dissemination to the foetus.

The following examples illustrate the invention without in any way limiting it.

EXAMPLE 1

Effect of Treatment of the Skin with Adhesive

Samples of human skin taken during plastic surgery are placed and fixed on a moist support. The adhesive (UHU cyanoacrylate glue) is deposited so as to cover the superficial surface of the skin and an adhesive strip (Tesa) is placed over it. The adhesive strip is then removed after 10-15 minutes of contact at ambient temperature. Nanoparticles of polystyrene 0.04 µm in diameter coated with "yellow-green fluorescent" molecules (Fluosphère®, Molecular probes, Oregon, USA) are applied to a surface area of 1 cm² for 18 hours at 37° C.

The skin is then treated more than three times in a row with the glue or simply once in order to estimate the effect of this treatment on the destruction of the corneal layer.

Each application of the adhesive in fact removes 30% of the corneal layer.

Figure 1:
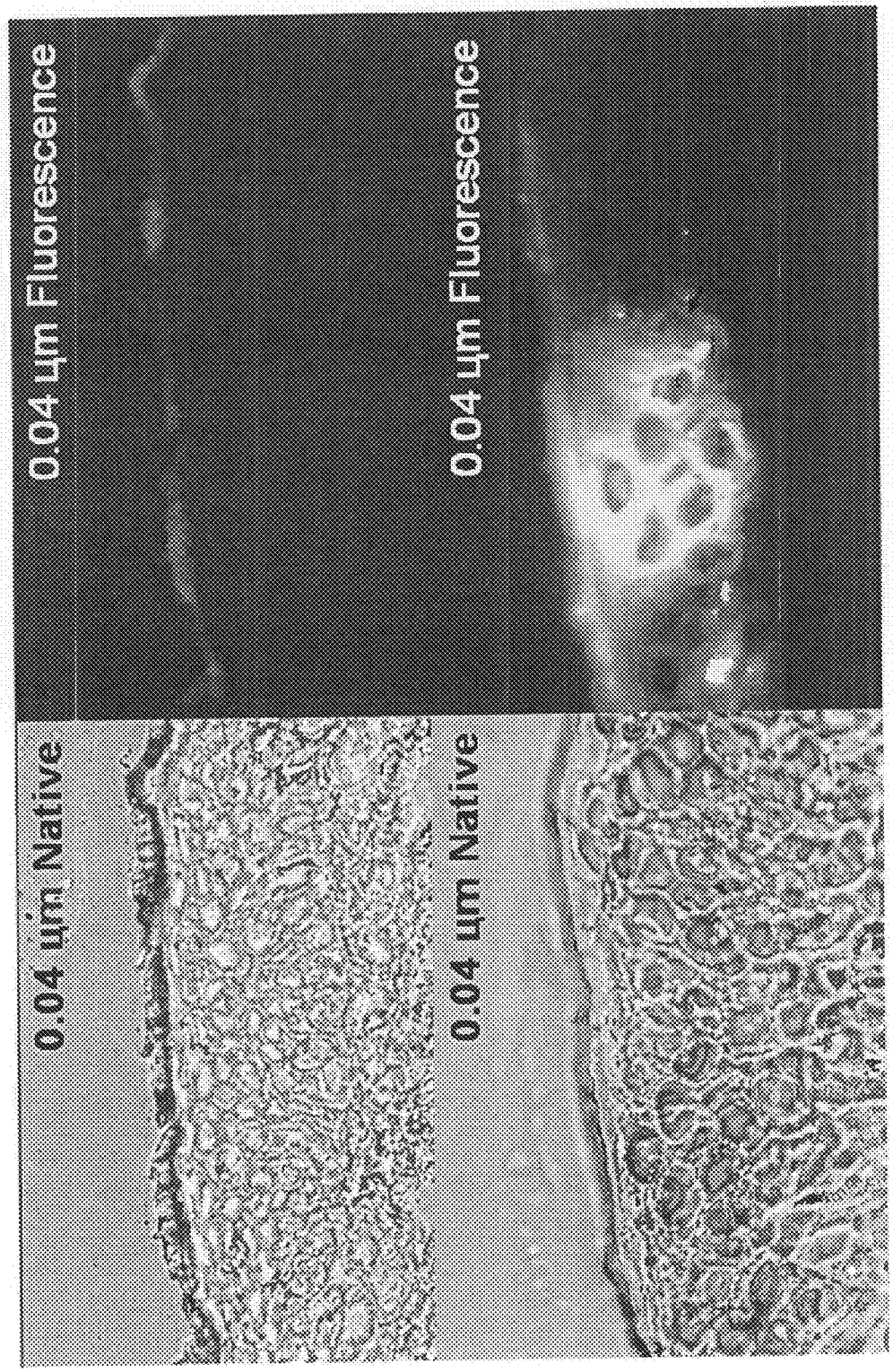

FIG. 1, bottom part, shows that the aggressive treatment of the skin using the cyanoacrylate glue (more than 3 applications of adhesive to the same surface area of skin) brings about the destruction of the corneal layer and also of the superficial part of the epidermis. The particles then cross the epidermis and diffuse into the layer of keratinocytes in a nonspecific manner.

The mild treatment of the skin with the cyanoacrylate glue (in this case, a single application of adhesive) results in only partial removal (less than or equal to 50%) of the corneal layer, as can be seen in the top part of FIG. 1.

EXAMPLE 2

Particle Size Specificity

The hair follicles originating from human skin explants removed after plastic surgery were opened using the method described above with a single application of adhesive. Solutions containing solid spherical beads, identical to those used in Example 1, but of various sizes (size from 1.5 to 0.04 µm), are sonicated for 3 minutes and then deposited on the pretreated skin, for 15 to 16 hours at 37° C. Adhesive strips were then applied so as to remove the remainder of the beads at the surface. The skin sample is then frozen in liquid nitrogen and sections 5 microns thick are then prepared by cutting from the dermis to the epidermis. Confocal microscopy techniques using a scanner visualize the penetration of the 0.04 µm beads.

Figure 2:
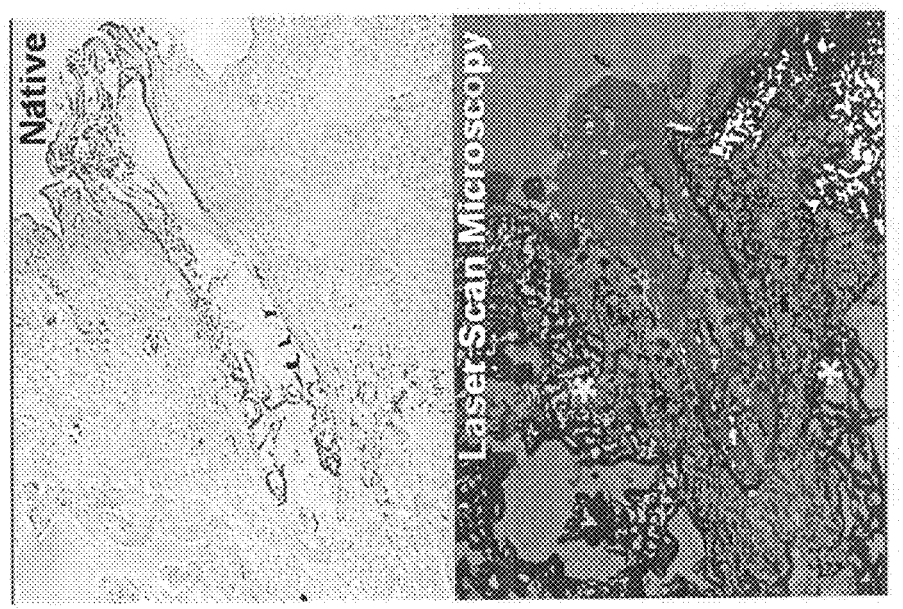
FIG. 2 shows the deep penetration of the fluorescent particles 0.04 µm in size in the hair follicles. The asterisks represent the adjacent tissue.
Figure 3:
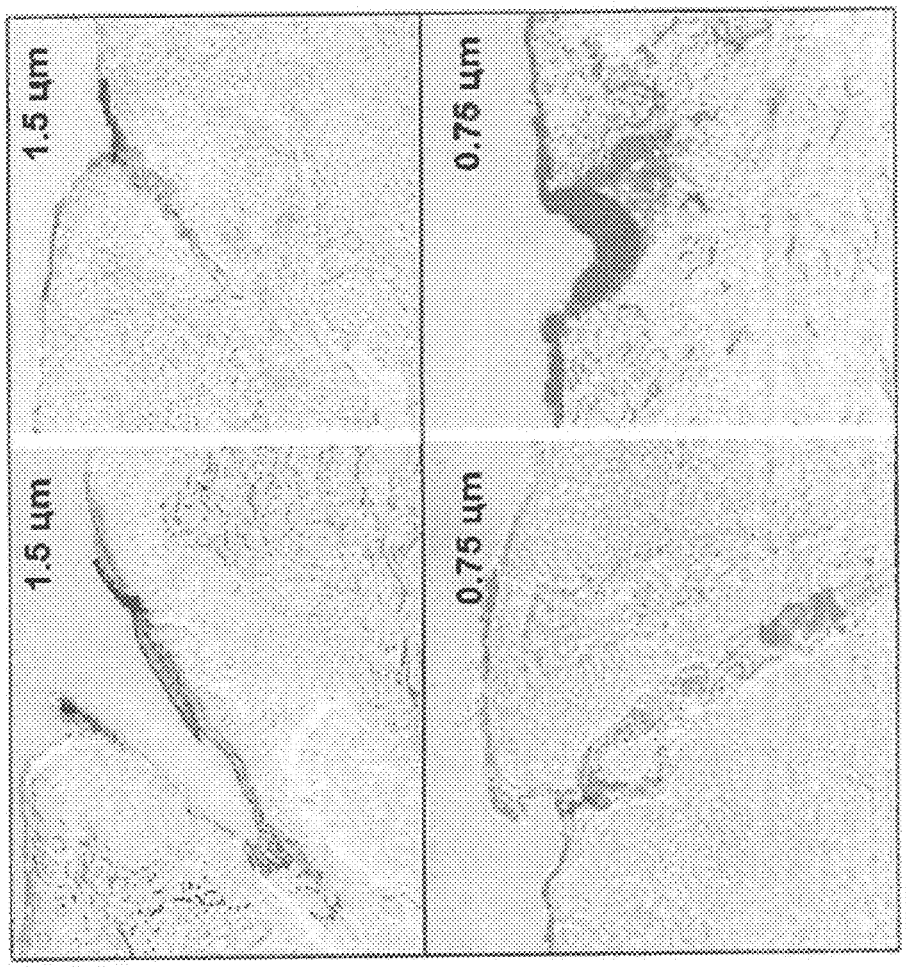
FIG. 3 shows the penetration of particles of various sizes of 1.5 and of 0.75 µm in the superficial part of the hair follicles.

FIG. 2 shows that the 0.04 µm beads penetrate deeply into the hair follicles and persist after successive washes, whereas beads having a size of the order of 0.75 µm remain at superficial levels of the hair follicle pathway (FIG. 3).

EXAMPLE 3

Location of Langerhans Cells

After a saturation step using a protein solution (DAKO protein block, Dako), frozen sections of human skin are incubated in a solution of anti-CD1a antibodies (1/50 dilution, Dako), which is an antibody specific for Langerhans cells and for dendritic cells. These cells in fact specifically express CD1a molecules.

The sections are washed in phosphate buffer (PBS pH 7.4) and then incubated in a solution of anti-mouse immunoglobulin antibodies (1/50 dilution, Vector Laboratories, Burlingame, Calif., USA) coupled to fluorescein, for 45 minutes. After washing, the slides are mounted in a VECTASHIELD mounting solution (Vector Laboratories, Burlingame, Calif., USA).

The specific labelling of these Langerhans cells makes it possible to visualize their location by fluorescence microscopy. FIG. 4 shows that the lower region of the hair follicles is particularly rich in markers for Langerhans cells (antigen-presenting cells of the epidermis) and for dendritic cells (epidermis and dermis).

EXAMPLE 4

Targeting of Beads to Langerhans Cells

The above example showed that the fluorescent particles diffuse to proximal regions rich in antigen-presenting cells (APCs). The majority of Langerhans cells, which are part of the APCs, in fact line this region surrounding the hair follicles.

The skin is treated by means of the hair follicle opening technique described above after a single application of the cyanoacrylate adhesive. A solution containing an amount of $2.5 \times 10^{12}$ solid spherical particles 0.04 μm in size, labelled with fluorescein, is sonicated for 3 minutes and then deposited onto the pretreated skin, for 15 to 16 hours at 37° C. A digestion is carried out for 18 hours in a solution of dispase (2.4 U/ml, Dispase I, Roche) at 37° C., followed by trypsinization (0.025% trypsin (Sigma) and 1.5 mM of $CaCl_2$ in PBS, at pH 7.4) for 10 minutes at 37° C., before resuspending the skin cells in RPMI 1640 (Gibco, Scotland) containing 15% foetal calf serum (Paa Gmbh, Austria), penicillin and streptomycin. The Langerhans cells present in the cell suspension are then purified using anti-CD1c antibodies by means of the bead purification method according to the manufacturer's indications (MACS®, Miltenyi).

The purified cells are then deposited on a slide. FIG. 5 shows that the presence of spherical particles of 0.04 μm is observed by fluorescence microscopy in the cell cytoplasm of the Langerhans cells.

EXAMPLE 5

Method of Transcutaneous Vaccination in Murine Models

A solution of anaesthetic is prepared by diluting 30 μl of 2% xylasine (Bayer, Germany) and 160 μl of ketamine (Imalgène 500, Merial) in 1 ml of NaCl at a concentration of 9 g/l. Five- to eight-week-old C57BL6 mice having an $H-2K^b$ haplotype (Iffa-Credo, Charles River, France) are anaesthetized by injecting a dose of 10 μl per gram of mouse with this solution intraperitoneally. The hair is removed from the right flank using adhesive strips (Lyréco, France) on a surface area of approximately 1 $cm^2$. The hair follicles were opened after successive applications of adhesive strips (more than 10 applications in mice). This method makes it possible to open the hair pores by partially removing the corneal layer. The immunogenic vaccine preparation (10 μl of "TETAGRIP" commercial vaccine (Aventis Pasteur)) is then deposited on the region from which the hair has been removed, using a pipette, over a surface area of 0.5 $cm^2$. After a waiting period of 30 minutes to 1 hour necessary for the penetration of the vaccine preparation, a patch composed of salicylic acid (1.5%) (exfoliant and scrubbing active agent), of triclosan (0.3%) (antibacterial and antifungal agent), and of bisabolol (1%) (anti-inflammatory and soothing agent) (SVR, Lysanel patch, France) is applied for one hour.

The blood taken is treated under sterile conditions. Once diluted with 4 volumes of 1×PBS, the blood is sampled with a pipette and deposited slowly into a tube containing 1.5 ml of lymphocyte-separating medium or FICOLL (Eurobio, France). Centrifugation at 2200 rpm for 20 minutes at ambient temperature without braking makes it possible to obtain separation of the red blood cells, which sediment at the bottom of the tube, and the appearance of a ring containing the PBMCs (peripheral blood mononuclear cells). The cell suspension derived from the ring is centrifuged at 1500 rpm for 5 minutes. The peripheral blood cells are counted with a Mallassez haemocytometer using trypan blue.

The objective of the technique is to measure the amount of cells that respond against a given antigen. The interferon gamma (IFNγ) produced by the effector T lymphocyte cells (100 000 PBMCs/well) during the antigenic stimulation is thus captured for 48 hours using a monoclonal antibody specific for this interferon (capture antibody: anti-IFNγ (IgG1, clone DB-1; Diaclone) and measured using the ELISPOT-IFNγ technique (according to the manufacturer, Diaclone). The frequencies of the TETAGRIP vaccine-specific T immune cells are thus measured at various days after immunization (FIG. 6).

In order to study the effect of the transcutaneous vaccination on the in vivo proliferation of T lymphocytes, the ovalbumin (ova) antigen was used as an immunogenic agent. As a result, the proliferation of CD8+ T cells specific for the ovalbumin antigen can be followed in vivo, after adoptive transfer of anti-ova CD8 T cells labelled with a fluorescent molecule: CFSE (carboxyfluorescein 5-(and 6)-diacetate, succinimidyl ester).

Briefly, naive anti-ova CD8 lymphocytes, originating from the OT-1 mouse (congenic marker CD45.2, transgenic for the T cell receptor (TCR) specific for the OVA epitope [257-264] of ovalbumin in an H2-Kb genetic background) are labelled with CFSE and then injected intravenously into recipient mice (congenic marker CD45.1) vaccinated transcutaneously according to the protocol described above, either with the ovalbumin protein or with plasmid DNA encoding this protein. CFSE, detectable by flow cytometry, is a marker for cell division. It diffuses in the cytoplasm and becomes diluted over the course of the cell divisions, consequently leading to a decrease in its intensity. The mice are sacrificed 4 or 7 days after immunization and the lymph nodes are removed. A double labelling, CD8 and CD45.2, makes it possible to select the CD8+ lymphocyte population originating from the OT-1 mouse.

FIG. 7 shows that the cell proliferation in the immunized mice is significantly higher than that of the "control" mice that receive no antigen, whatever the form of immunogen used (protein or DNA).

The humoral immune response detected by the production of anti-ovalbumin antibodies is measured by means of antigen-specific ELISA assays after vaccination using the plasmid DNA encoding the ovalbumin antigen or the protein in the presence of adjuvant: cholera toxin. Briefly, C57BL6 mice are immunized either with 100 μg of ovalbumin protein (n=6), or 100 μg of ovalbumin protein with 10 μg of cholera toxin labelled with FITC (fluoroisothiocyanate), or 100 μg of plasmid DNA encoding the ovalbumin protein (n=8). The antibodies were assayed by the ELISA technique using sera originating from blood samples taken at D 14 after vaccination. The standard deviations are represented (FIG. 8).

EXAMPLE 6

Location of the Particles in a Murine Model

Particles in the form of fluorescent microbeads (Fluorosphere® of 0.04 μm) were applied to mouse skin according to the protocol described in Example 6. The fluorescence is visualized by means of the laser microscopy technique at various depths in the skin (Cell-Vizio®, MaunaKea technologies). This method also makes it possible to locate the particles at various times in vivo. Cell-Vizio™ is a system of confocal fluorescence fibre-optic microscopy. The first optical probe used for the image acquisition has a diameter of 1.5 mm (ref. S-1500-5.0); this probe makes it possible to obtain images immediately below the surface of a biological tissue, with a thickness of 15 μm and a lateral resolution of 5 μm. The following 2 probes have a diameter of 1.8 mm and enable an acquisition of 20 μm at a depth of 30 μm (ref. HD-1800-2.5/30) or 80 μm (ref. HD-1800-2.5/80) with a lateral resolution of 2.5 μm. During the acquisition period, at various times after application of the fluorospheres, the mice are under anaesthetic in order to prevent any movement. The area from which hair has been removed is wiped beforehand with a saline solution in order to clean away the residual impurities from the area, before affixing the various probes thereto. To analyze the lymph nodes, the fat is removed from the organ beforehand, before applying the probe to its surface.

1 to 5 hours after application of the microbeads to the skin, the latter are found in cavities in the corneal layer at a depth of 15 μm to 80 μm (FIG. 9A). After 24 hours, the fluorescence diffuses around the hair follicles in areas rich in APCs (FIG. 10A). However, there is no trace of fluorescence in other nontreated areas of the mouse (FIG. 10B). The microbeads are accumulated in the proximal lymph nodes and, to a lesser extent, in the distal lymph nodes with respect to the area treated (FIG. 11).

Thus, the microbeads are transported to the site of the immune response from 24 hours after transcutaneous application.

EXAMPLE 7

Measurement of the Specific Protective T Response

The mice were immunized by the method described according to Example 5, using DNA encoding ovalbumin. After vaccination, 200 000 tumour cells of the line expressing the ovalbumin antigen (EG-7) or not expressing it (EL-4) are injected subcutaneously on the left flank of the animals. The size of the tumour is measured at various times in the immunized animals.

FIG. 12 shows that the transcutaneous vaccination induces a protective immune response in 90% of the mice, which never develop a tumour at day 40, whereas all the control mice have already developed a tumour at day 22.

EXAMPLE 8

Immune Response Induction in Humans

This protocol was applied to seven normal volunteers who received, on the upper surface of the arm, the influenza A and B vaccine (Agrippal® Chiron, France) transcutaneously, either over a surface area of 16 cm² or over a surface area of 32 cm² of skin. The application was carried out at ambient temperature. The Agrippal® vaccine consists of purified antigens and not of inactivated whole viruses. The volunteers remained seated in the test chamber before application, for 30 minutes, and also during the incubation periods between the various steps of the application. After the application of vaccine, the volunteers were warned not to take a shower or a bath and to avoid any activity which could cause sweating or a mechanical stress at the site of investigation, i.e. physical exercise, for 24 hours following the application of the vaccine. Four individuals were also vaccinated intramuscularly. All the volunteers signed an informed consent form. The volunteers were monitored for the first week after administration as regards side effects such as abnormal redness of the skin, an itching sensation, a sensation of pain or stinging during the five minutes after application, or a loss of stratum corneum.

At the moment of application, the left arm of the volunteers was kept at 90° and positioned horizontally on an area made of plastic, the external upper part of the arm facing upwards. The arm was kept in this position throughout the period of application. One or two squares of 4×4 cm were delimited on the external upper part of the left arm of the volunteers by means of a plastic matrix. The sites of investigation were then delimited using a permanent marker (skin marker H7003, Falc).

The down was shaved on the sites of investigation and also on the portion of neighbouring skin (2 cm on either side of each site of investigation) using a dry razor (Disposable Hospital Razor, Art-Nr.: 182 h, Wilkinson Sword GmbH, Solingen, Germany).

After shaving, the cyanoacrylate glue (superglue, UHU GmbH & Co., KG, Buehl/Baden, Germany) was applied dropwise (9 drops, i.e. approximately 190 mg) to each site of investigation. A glass microscope slide was used to spread the glue uniformly on the sites of investigation. Immediately after spreading, an adhesive strip (6×5 cm, No. 57176-00000, 66 m×50 mm, Tesa® Beiersdorf, Beiersdorf, Germany) was placed on the site of investigation. A sheet of paper (21×7 cm) was placed over the strip and a rubber was rolled around the sites of investigation in order to avoid air bubbles at the surface of the skin. After 20 minutes, the scotch and adherent glue were rapidly removed from the surface of the skin. p Pulling off skin surface with cyanoacrylate removes the keratinized material, the lipids and other cell debris and approximately 30% of the stratum corneum. The remaining stratum corneum and the viable epidermis are left intact.

Next, the sites of investigation were delimited with a barrier of silicone (Window-Colour-Konturpaste, N° 4469/ko, Max-Bringmann GmbH & Co., Wendelstein, Germany) so as to avoid dissemination of the soluble vaccine subsequently applied. The silicone barrier must dry for 20 minutes. During this incubation period, the volunteers remained seated and the left arm remained in its position.

For an application over a surface area of 32 cm², 250 μl of Agrippal® vaccine are applied dropwise using the syringe provided by the manufacturer, to the surface of the skin of each site of investigation. For application over a surface area of 16 cm², the same amount of vaccine was applied twice. This procedure is followed by incubation for 20 minutes. A hydrocolloid dressing (Comfeel® Plus Transparent 9×14 cm Art.-Nr.: 3542, Coloplast A/S, Denmark) is then applied for 24 hours in order to protect the sites of investigation.

15 ml of peripheral blood were then collected and the peripheral blood mononuclear cells were isolated with Ficoll. All the immunological investigations were carried out on fresh cells and frozen serum.

The ELISpot-IFNγ detection for the human PBMCs (peripheral blood mononuclear cells) was carried out as previously described (Combadiere et al., JEM). Briefly, 96-well ELISpot plates (Millipore, Molsheim, France) were coated with an anti-human IFNγ antibody (IgG1/B-B1, Diaclone, Strasbourg, France). After having blocked with 10% foetal calf serum, wells in triplicate were filled with $10^5$ freshly isolated PBMCs. The plates were incubated at 37° for 20 hours with 0.45 mg/ml of Agrippal® vaccine (Chiron). PHA (Abbott, Rungis, France) and medium alone were used as positive and negative controls, respectively. The wells were then washed and the spots detected after the addition of an anti-human IFNγ antibody coupled to biotin (B-G1, Diaclone) for 4 hours at 37° C., followed by incubation with alkaline phosphatase-coupled streptavidin for 1 hour at 37° C., followed by visualization with 5-bromo-4-chloro-3-indolyl phosphate/4-nitrobluetetrazolium (Sigma-Aldrich, Saint-Quentin, France). The plates were incubated at ambient temperature until the spots appeared. The cells forming spots specific for the antigen (SFCs) were counted with an automatic microscope (Zeiss, Le Pecq, France). The samples were considered to be positive upon detection of at least 50 SFCs per million PBMCs above the base level.

Results:

No side effect was observed in the following volunteers.

Because all the volunteers received the same amount of vaccine (0.5 ml of Agrippal®), we compared the cellular immune response against the influenza B vaccine at days 0, 14 and 28 for all the volunteers (FIGS. 13 and 14A & B). The FIG. 13 shows that significant cellular responses can be observed with either the transcutaneous route of administration or the intramuscular route of administration.

FIGS. 14A and 14B show that significantly increased cellular responses were observed at day 14 (n=7, p<0.05) and at day 28 (n=6, p<0.05). This test in fact makes it possible to detect CD4 and CD8 effector T cells directed against the influenza proteins.

At day 0, in certain individuals, the amount of effector T cells is above the base level (50 SFU/million PBMC) suggesting a pre-existing immunity to influenza B (FIGS. 13 and 14). Advantageously, an increased T cell response subsequent to the vaccination was also observed in some of these individuals, confirming the effectiveness of transcutaneous vaccination in humans.

In conclusion, transcutaneous vaccination with the Agrippal® vaccine results in an induction of the immune response in the volunteers tested.

EXAMPLE 9

Transcutaneous Vaccination Induced Both CD4 and CD8 Cell Responses while Intramuscular Vaccination Induces Only CD4 Response The production of IFNγ by CD4 and CD8 cell populations was assayed using flow cytometric analysis, after a short-term (16 hours) stimulation of PBMCs with "Agrippal" vaccine. The transcutaneous administration of Aggripal vaccine has been done as previously explained. The intramuscular injection of Agrippal® vaccine (0.5 ml) as provided by the manufacturer were injected intramuscularly into the Musculus deltoideus of the left arm after careful disinfection, according to Good Clinical Practice.

Briefly, frozen PBMCs were thawed in RPMI (Life Technologies, Cergy Pontoise, France) containing 5% FCS (Seromed, Germany), 2 mmol/L L-glutamine (Gibco BRL, Life Technology, Paisley, Scotland) and antibiotics (1000 UI/mL penicillin sodium, 1 mg/mL streptomycin sulfate, and 250 ng/mL amphotericin B). Cells were stimulated with 1 μg/mL of PHA for 12 hours at 37° C. Brefeldin A (5 μg/ml) (Sigma Chemical Co., City, France) was to the well 4 hours before harvesting in order to detect intracellular cytokines. Cells were then stained with PC7-conjugated antibodies against CD4 or CD8 (Beckman Coulter, City, Country) washed in PBS and fixed in 4% PFA for 20 min. Cells were then permeabilized with PBS 5% FCS 0.1% saponin before addition of anti-IFNγ specific antibodies. At least 1,000,000 live events according to forward and side scatter parameters, were accumulated and analyzed with Cell-Quest Pro software (Becton Dickinson, City, Country).

FIG. 15A shows that the percentage of IFNγ producing CD4 cells increase after both transcutaneous and intramuscular vaccination at day 14 and day 28. The increase in CD4 cell response was significant after transcutaneous vaccination at day 28 compared to day 0. It was also significantly different after conventional intramuscular injection at day 14 and 28 compared to day 0. These vaccinations seem to induce similar C4 effector cells responses in all individuals.

FIG. 15B shows an increase in influenza-specific CD8+ IFNγ+ cells at day 14 in individuals who had received transcutaneous vaccination, while CD8 responses were undetectable in all volunteers who were vaccinated by intramuscular injection.

FIG. 16 shows representative flow cytometric analysis for CD4 and CD8 cells of one volunteer, who received vaccine transcutaneously. This figure confirms that both CD4 and CD8 cells are induced by this vaccination route.

The results show that only transcutaneous vaccination induced both CD4 and CD8 cellular response, whereas intramuscular vaccination induced more prominent CD4, but no CD8 cellular responses.

The invention claimed is:

1. A method of administering a vaccine preparation comprising particles, the method comprising:
   pretreating the surface of a skin to which the vaccine preparation is to be administered by applying adhesive strips or instantaneous adhesive or glue to the surface of the skin in order to improve the opening of hair follicles by ablation of at most 50% of the corneal layer; and
   transcutaneously contacting the skin with the particles, wherein the particles have at least a cross section having a diameter of 0.1 nm to 0.2 μm after possible deformation;
   wherein the particles enter the hair follicles and, due to the diameter of the particles, diffuse through the epithelium of the hair follicles, resulting in an induction, stimulation or increase of a protective immune response.

2. The method according to claim 1, wherein the particles have at least a cross section having a diameter of 0.1 nm to 0.1 μm after possible deformation.

3. The method according to claim 1, wherein the particles have at least a cross section having a diameter of 0.1 nm to 0.05 μm after possible deformation.

4. The method according to claim 1, wherein the particles are solid particles.

5. The method according to claim 1, wherein the particles are viral particles.

6. The method according to claim 1, wherein the pretreating is carried out using adhesive strips.

7. The method according to claim 1, wherein the pretreating is carried out by application of instantaneous adhesive or glue to the surface of the skin.

8. The method according to claim 1, wherein the particles are wax beads.

9. The method according to claim 1, wherein the particles comprise polyethyleneimine or polylactic acid.

10. The method according to claim 1, wherein the particles comprise an antigen selected from the group consisting of a protein, a peptide, a polysaccharide, a polyoside, a lipopolysaccharide, a toxoid, a conjugated carrier protein, a cell extract, a viral extract, a bacterial extract, a parasitic extract, a live recombinant viral particle, a live bacterial particle, a live parasitic particle, an attenuated viral particle, an attenuated bacterial particle, an attenuated parasitic particle, a killed viral particle, a killed bacterial particle, a killed parasitic particle, an inactivated viral particle, an inactivated bacterial particle, an inactivated parasitic particle, a recombinant viral particle, a recombinant bacterial particle, a recombinant parasitic particle, a viral pseudoparticle, DNA, a recombinant nucleic acid of a pathogen, and a cancer cell extract.

11. The method according to claim 1, wherein the particles comprise at least one adjuvant selected from the group consisting of cytokines, of a chemokine, a growth factor, a pathogen derivative, a toxoid, an oily emulsion, a lipid, a lipopolysaccharide, a copolymer, a PAM, a toll-like receptor ligand, MPL-A, Quil-A, ISCOM ,Dimethyl Dioctadecyl ammonium bromide (DDAB), Dimethyl Dioctadecyl ammonium chloride (DDAC), a CpG motif, Leif, a detoxified toxoid, and a nondetoxified toxoid.

12. The method according to claim 1, wherein the particles comprise naked DNA encoding a part of a HIV genome.

13. The method according to claim 5, wherein the viral particles are particles of an attenuated poxvirus.

14. The method according to claim 1, wherein the particles comprise nanoparticles of polylactic acid loaded with one or more of a peptide, a protein, DNA or a nucleic acid.

15. The method according to claim 1, wherein the protective immune response is a protective immune CD8 T cells response.

16. The method according to claim 1, wherein the induction, stimulation or increase of a protective immune response is effected in an immuno suppressed individual.

17. The method according to claim 1, wherein the particles are viral particles and have at least a cross section having a diameter of 0.1 nm to 0.1 µm after possible deformation.

18. The method according to claim 1, comprising applying an instanstaneous glue to the surface of the skin and an adhesive strip over the glue.

19. The method according to claim 18, wherein the applying is performed one time.

20. The method according to claim 18, wherein the applying is performed three times in a row.

* * * * *

UNITED STATES PATENT AND TRADEMARK OFFICE
CERTIFICATE OF CORRECTION

PATENT NO. : 8,956,617 B2  
APPLICATION NO. : 11/993737  
DATED : February 17, 2015  
INVENTOR(S) : Behazine Combadiere et al.

Page 1 of 1

It is certified that error appears in the above-identified patent and that said Letters Patent is hereby corrected as shown below:

Column 6, line 40, "1000 μg" should read --1000 μm--.

Column 14, line 29, delete "p" after skin.".

Column 16, line 8, "C4" should read --CD4--.

Column 18, line 6, "immuno suppressed" should read --immunosuppressed--.

Signed and Sealed this  
Thirteenth Day of October, 2015

Michelle K. Lee  
*Director of the United States Patent and Trademark Office*